United States Patent
Smirnov

(10) Patent No.: US 12,171,691 B2
(45) Date of Patent: Dec. 24, 2024

(54) SYSTEMS AND METHODS FOR CROSS-LINKING TREATMENTS OF AN EYE

(71) Applicant: Avedro, Inc., Waltham, MA (US)

(72) Inventor: Mikhail Smirnov, North Andover, MA (US)

(73) Assignee: Avedro, Inc., Waltham, MA (US)

( * ) Notice: Subject to any disclaimer, the term of this patent is extended or adjusted under 35 U.S.C. 154(b) by 609 days.

(21) Appl. No.: 17/434,275

(22) PCT Filed: Feb. 26, 2020

(86) PCT No.: PCT/US2020/019857
§ 371 (c)(1),
(2) Date: Aug. 26, 2021

(87) PCT Pub. No.: WO2020/176598
PCT Pub. Date: Sep. 3, 2020

(65) Prior Publication Data
US 2022/0133533 A1    May 5, 2022

Related U.S. Application Data

(60) Provisional application No. 62/810,509, filed on Feb. 26, 2019.

(51) Int. Cl.
*A61F 9/00* (2006.01)
*A61F 9/007* (2006.01)
(Continued)

(52) U.S. Cl.
CPC .. *A61F 9/0079* (2013.01); *A61F 2009/00872* (2013.01); *A61F 2009/00893* (2013.01); *A61N 5/062* (2013.01)

(58) Field of Classification Search
CPC .. A61F 2009/00872; A61F 2009/00893; A61F 9/0079; A61N 5/062
See application file for complete search history.

(56) References Cited

U.S. PATENT DOCUMENTS 4,034,750 A   7/1977   Seiderman
4,665,913 A   5/1987   L'Esperance, Jr.
(Continued)

FOREIGN PATENT DOCUMENTS

DE   102008046834   3/2010
EP       1561440     8/2005
(Continued)

OTHER PUBLICATIONS

Extended European Search Report for related European Application No. 20763130.0; action dated Oct. 21, 2022; (9 pages).
(Continued)

*Primary Examiner* — Amanda K Hulbert
(74) *Attorney, Agent, or Firm* — K&L Gates LLP

(57) ABSTRACT

An example system for corneal treatment includes an illumination system to generate cross-linking in at least one selected region of a cornea treated with a cross-linking agent by delivering photoactivating light according to one or more photoactivation parameters. The system includes a controller to receive input relating to one or more treatment parameters, which include the one or more photoactivation parameters. The controller is configured to output information for adjusting the one or more treatment parameters by (A) determining from the input, a distribution of cross-links for the at least one selected region of the cornea; (B) determining, from the distribution of cross-links, a shape change for the cornea; and (C) determining, from the shape change for the cornea, a change in vision for the subject. Responsive to the output from the controller, the illumination system is configured to adjust at least one of the one or more photoactivation parameters.

18 Claims, 6 Drawing Sheets

(51) Int. Cl.
    *A61F 9/008*     (2006.01)
    *A61N 5/06*      (2006.01)

(56) References Cited

U.S. PATENT DOCUMENTS

| | | |
|---|---|---|
| 4,712,543 A | 12/1987 | Baron |
| 4,764,007 A | 8/1988 | Task |
| 4,891,043 A | 1/1990 | Zelmer et al. |
| 4,969,912 A | 11/1990 | Kelman et al. |
| 4,994,058 A | 2/1991 | Raven et al. |
| 5,019,074 A | 5/1991 | Muller |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,624,437 A | 4/1997 | Freeman et al. |
| 5,779,696 A | 7/1998 | Berry et al. |
| 5,786,893 A | 7/1998 | Fink et al. |
| 5,891,131 A | 4/1999 | Rajan et al. |
| 5,910,110 A | 6/1999 | Bastable |
| 6,033,396 A | 3/2000 | Huang et al. |
| 6,139,876 A | 10/2000 | Kolta |
| 6,161,544 A | 12/2000 | DeVore et al. |
| 6,188,500 B1 | 2/2001 | Rudeen et al. |
| 6,218,360 B1 | 4/2001 | Cintron et al. |
| 6,270,221 B1 | 8/2001 | Liang et al. |
| 6,280,436 B1 | 8/2001 | Freeman et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,394,999 B1 | 5/2002 | Williams et al. |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,617,963 B1 | 9/2003 | Watters et al. |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,331,350 B2 | 2/2008 | Kochevar et al. |
| 7,402,562 B2 | 7/2008 | DeWoolfson et al. |
| 7,731,362 B2 | 6/2010 | Gerlach |
| 7,753,943 B2 | 7/2010 | Strong |
| 7,898,656 B2 | 3/2011 | Yun et al. |
| 7,935,437 B2 | 5/2011 | Dupps et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0055095 A1 | 12/2001 | D'Souza et al. |
| 2002/0013577 A1 | 1/2002 | Frey et al. |
| 2002/0159618 A1 | 10/2002 | Freeman et al. |
| 2002/0164731 A1 | 11/2002 | Nishihara et al. |
| 2003/0175259 A1 | 9/2003 | Karageozian et al. |
| 2003/0189689 A1 | 10/2003 | Rathjen |
| 2003/0231285 A1 | 12/2003 | Ferguson |
| 2004/0002694 A1 | 1/2004 | Pawlowski et al. |
| 2004/0093046 A1 | 5/2004 | Sand |
| 2004/0199079 A1 | 10/2004 | Chuck et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0195076 A1 | 8/2006 | Blumenkranz et al. |
| 2006/0276777 A1 | 12/2006 | Coroneo |
| 2007/0024860 A1 | 2/2007 | Tobiason et al. |
| 2007/0048340 A1 | 3/2007 | Bran et al. |
| 2007/0123845 A1 | 5/2007 | Lubatschowski |
| 2007/0135805 A1 | 6/2007 | Peyman |
| 2007/0142828 A1 | 6/2007 | Peyman |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0116096 A1 | 5/2009 | Zalevsky et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0234335 A1 | 9/2009 | Yee |
| 2009/0275929 A1 | 11/2009 | Zickler |
| 2010/0028407 A1 | 2/2010 | Del Priore et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0204584 A1 | 8/2010 | Ornberg et al. |
| 2010/0210996 A1 | 8/2010 | Peyman |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0288466 A1 | 11/2011 | Muller et al. |
| 2011/0301524 A1 | 12/2011 | Bueler et al. |
| 2012/0083772 A1 | 4/2012 | Rubinfield et al. |
| 2012/0203161 A1 | 8/2012 | Herekar |
| 2012/0215155 A1 | 8/2012 | Muller et al. |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2014/0194957 A1 | 7/2014 | Rubinfield et al. |
| 2014/0249509 A1 | 9/2014 | Rubinfield et al. |
| 2016/0162630 A1 | 6/2016 | Studer et al. |
| 2016/0310319 A1* | 10/2016 | Friedman ............ A61F 9/0079 |

FOREIGN PATENT DOCUMENTS

| | | |
|---|---|---|
| EP | 1790383 | 5/2007 |
| IT | MI2010 | 5/2010 |
| JP | 2007-523674 A | 8/2007 |
| JP | 2014-518643 A | 8/2014 |
| JP | 2014519866 A | 8/2014 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 2005110397 | 11/2005 |
| WO | 2006012947 | 2/2006 |
| WO | 2006128038 | 11/2006 |
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |

(56) References Cited

FOREIGN PATENT DOCUMENTS

| WO | 2008095075 | 8/2008 |
|---|---|---|
| WO | 2009073213 | 6/2009 |
| WO | 2009114513 | 9/2009 |
| WO | 2009146151 | 12/2009 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |

OTHER PUBLICATIONS

Studer, et al; "Biomechanical model of human cornea based on stromal microstructure"; Journal of Biomechanics; Nov. 2009; (7 pages).
Notification of Reason for Rejection from corresponding Japanese Patent Application No. 2021-549800, mailed Aug. 22, 2023.
Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).
Rolandi et al. Correlation of Collagen-Linked Fluorescence and Tendon Fiber Breaking Time. Gerontology 1991;27 :240-243 (4 pages).
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Artificial Stiffening of the Cornea by Induction of Intrastromal Cross-links," Oer Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E., et al., "Techniques for Stiffening the Cornea," Journal of Refractive Surgery, vol. 15, Issue 6, pp. 711-713; Nov.-Dec. 1999 (4 pages).
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thorton, I. et. al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.
UV-X: Radiation System for Treatment of Keratokonus, Peschke Meditrade GmbH; retrieved from http://www.peschkemed.ch/ on Sep. 27, 2011 (1 page) (date unknown, prior to Sep. 16, 2008).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).
Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin I ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970).
Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 5, 2011 (pp. 13011-13022).
International Patent Application No. PCT/US2020/019857, International Search Report, Jun. 4, 2020 (2 pages).
International Patent Application No. PCT/US2020/019857, Written Opinion of the ISA, Jun. 4, 2020 (4 pages).
Staffan Schedin, Per Hallberg, and Anders Behndig, "Analysis of long-term visual quality with numerical 3D ray tracing after corneal crosslinking treatment," Appl. Opt. 56, 9787-9792 (2017) (Abstract).
Notice of Reasons for Rejection for Japanese Patent Application No. 2014-549800 dated Jan. 10, 2023.
Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).
Averianova, O. S., "Nastoyaschee I buduschee kross-linkage." Mir Ofalmologii, 2010, [online] [retrieved on Feb. 13, 2014] Retrieved from the internet: http:/ /miroft.org.ualpublications/.html.
Baier J. et al., "Singlet Oxygen Generation by UVA Light Exposure of Endogenous Photosensitizers," Biophysical Journal, vol. 91(4), pp. 1452-1459; Aug. 15, 2006 (8 pages).
Ballou, D. et al., "Direct Demonstration of Superoxide Anion Production During The Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).
Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).
Bruel, A., "Changes In Biomechanical Properties, Composition of Collagen and Elastin, and Advanced Glycation Endproducts of The Rat Aorta In Relation to Age," Atherosclerosis 127, Mar. 14, 1996 (11 pages).

(56) References Cited

OTHER PUBLICATIONS

Chace, K.V. et al., Abstract for "The role of nonenzymatic glycosylation, transition metals, and free radicals in the formation of collagen aggregates", Arch Biochem Biophys., 1991, Aug. 1, 288(2) pp. 473-480 (1 page).
Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).
Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).
Erskine H., "Avedro Becomes Sponsor of US FDA Clinical Trials of Corneal Collagen Crosslinking," Press Release, Mar. 16, 2010 (1 page).
Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).
Friedman, M. et al. "Advanced Corneal Cross-Linking System with Fluorescence Dosimetry", Journal of Ophthalmology, vol. 2012, Article ID 303459, dated May 7, 2012 (6 pages).
Gibson, Q. et al., "The Oxidation of Reduced Flavin Mononucleotide by Molecular Oxygen," Biochem. J. (1962) 83, 368-377 (10 pages).
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).
Hitzenberger et al., "Birefringence Properties of The Human Cornea Measured With Polarization Sensitive Optical Coherence Tomography," Bull. Soc. Beige Ophtalmol., 302, 153-168, 2006.
Holmstrom, B. et al., "Riboflavin as an Electron Donor In Photochemical Reactions," 1867-1871, Nov. 29, 1960 (5 pages).
IMEX, "KXL System: Crosslinking Para Cirugia Corneal Bibliografia Cientifica," Product Literature, Nov. 23, 2010 (24 pages).
Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UV A-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in JVNRiboflavin Corneal Collagen Cross-Linking," Current Eye Research 35(8), pp. 715-721; Mar. 2010 (7 pages).
Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).
Koller, T. et. al., "Complication and failure rates after corneal crosslinking," Journal Cataract and refractive surgery, vol. 35, No. 8, Aug. 2009, pp. 1358-1362.
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pts. 17-26).
Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Marzouky, et. al., Tensioactive-mediated Transepithelial Corneal Cross-linking—First Laboratory Report, European Ophthalmic Review, 2009, 3(2), pp. 67-70.
Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Meek, K.M. et al. "The Cornea and Sclera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Pinelli R., et al., "C3-Riboflaving Treatments: Where Did We Come From? Where are We Now?" Cataract & Refractive Surgery Today Europe, Summer 2007, pp. 36-46; Jun. 2007 (10 pages).
Pinelli, R. "Corneal Cross-Linking with Riboflavin: Entering a New Era in Ophthalmology." Ophthalmology Times Europe. vol. 2, No. 7, Sep. 1, 2006 (3 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).
Reinstein, D. Z. et al. "Epithelial Thickness Profile as a Method to Evaluate the Effectiveness of Collagen Cross-Linking Treatment

(56) References Cited

OTHER PUBLICATIONS

After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

\* cited by examiner

SYSTEMS AND METHODS FOR CROSS-LINKING TREATMENTS OF AN EYE

CROSS REFERENCE TO RELATED APPLICATIONS

This application is a National Stage Application of International Patent Application No. PCT/US2020/019857, filed Feb. 26, 2020, which claims priority to, and benefit of, U.S. Provisional Patent Application Ser. No. 62/810,509, filed Feb. 26, 2019, the contents of these applications being incorporated entirely herein by reference.

BACKGROUND OF THE INVENTION

Field of the Invention

The present disclosure pertains to systems and methods for treating disorders of the eye, and more particularly, to systems and methods for cross-linking treatments of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, astigmatism, irregular astigmatism, presbyopia, etc.

SUMMARY

According to aspects of the present disclosure, an example system for corneal treatment for a subject includes an illumination system including a light source and optical elements. The illumination system is configured to generate cross-linking in at least one selected region of a cornea treated with a cross-linking agent by delivering photoactivating light to the at least one selected region of the cornea according to one or more photoactivation parameters. The system includes a controller configured to receive input relating to one or more treatment parameters. The one or more treatment parameters include the one or more photoactivation parameters. The controller is configured to execute program instructions stored on one or more non-transitory computer-readable storage media to output information for adjusting the one or more treatment parameters. The program instructions include:

(A) a first set of program instructions that determines, from the input relating to the one or more treatment parameters, a distribution of cross-links for the at least one selected region of the cornea;

(B) a second set of program instructions the determines, from the distribution of cross-links, a shape change for the cornea; and (C) a third set of program instructions that determines, from the shape change for the cornea, a change in vision for the subject.

In response to the output from the controller, the illumination system is configured to adjust at least one of the one or more photoactivation parameters for delivering the photoactivating light.

In the example system above, the one or more treatment parameters may include at least one of a soak time for the cross-linking agent, a pulse duration for the photoactivating light, an irradiance of the photoactivating light, a dose of the photoactivating light, an illumination pattern for the photoactivating light, or a concentration of oxygen applied to the cornea.

In the example system above, the first set of program instructions may determine the distribution of cross-links from (i) reactions involving reactive oxygen species (ROS) including at least singlet oxygen, peroxides, superoxides, and hydroxyl radicals, and (ii) reactions not involving oxygen.

In the example system above, the second set of program instructions may determine (i) a pre-treatment state of the cornea based on a pre-treatment shape and a pre-treatment intraocular pressure of the cornea, and (ii) the shape change for the cornea based on the pre-treatment state of the cornea and the distribution of cross-links.

In the example system above, the third set of program instructions may determine the change in vision for the subject based on a ray trace model of image formation on a retina in response to the shape change for the cornea.

The example system above may further include an oxygen source and an oxygen delivery device configured to provide a concentration of oxygen from the oxygen source to the at least one selected region of the cornea, wherein the one or more treatment parameters further relates to the concentration of oxygen.

In the example system above, the second set of program instructions may determine the shape change for the cornea according to a biomechanical model that models corneal elasticity and a stiffening associated with cross-links. The controller may be further configured to calibrate the biomechanical model by calibrating, based on measured reference data, variable model parameters relating to the corneal elasticity and the stiffening associated with cross-links. The variable model parameters may include elasticity parameters associated with isotropic material in a stroma of the cornea and stiffness parameters associated with anisotropic material in the stroma, and the controller may calibrate the elasticity parameters and the stiffness parameters according to measurements of apex rise associated with intraocular pressure. The variable model parameters may include stiffening factors associated with cross-links, and the controller may calibrate the stiffening factors according to measurements of keratometry.

DESCRIPTION

Figure 1:
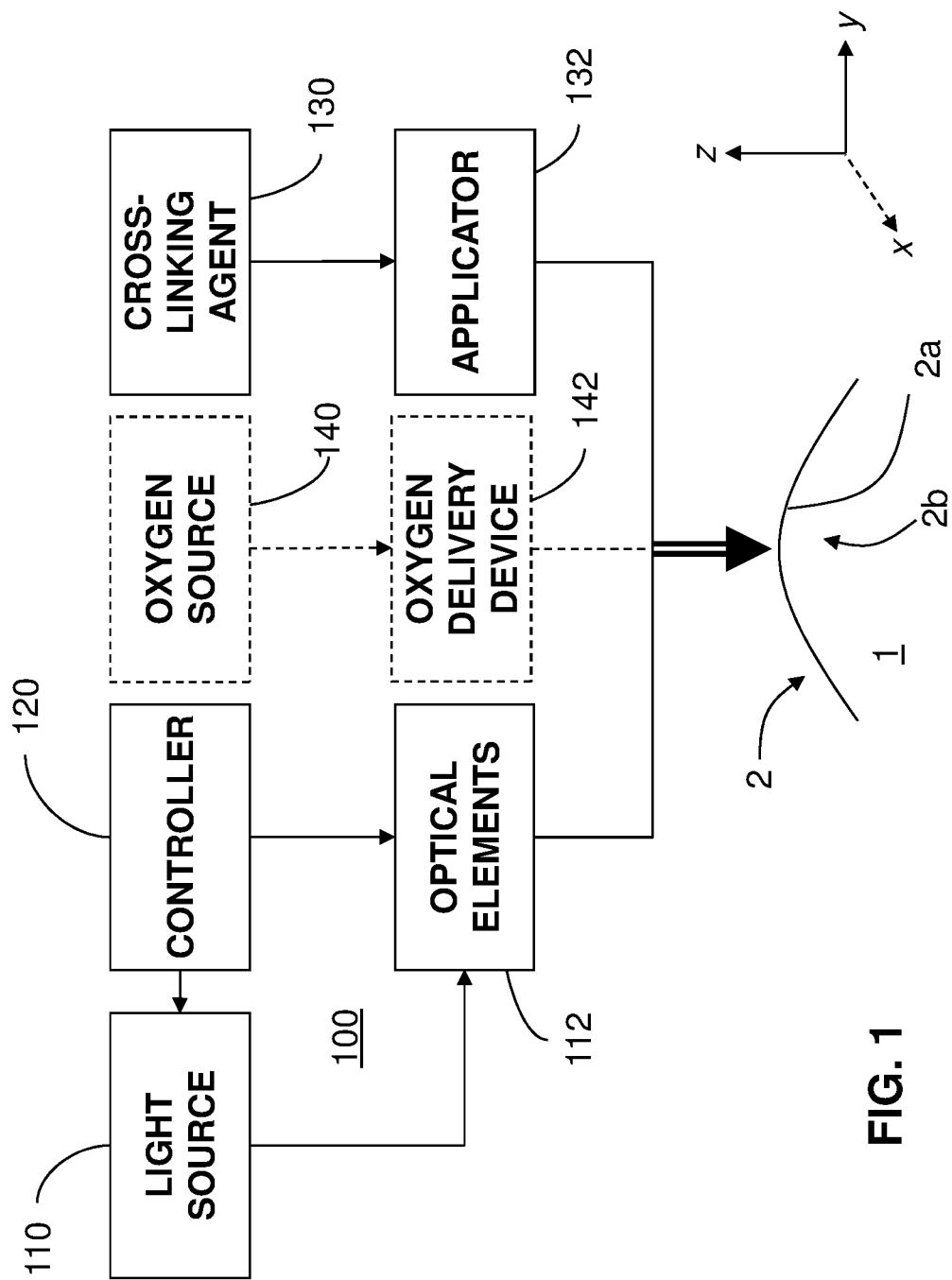
FIG. 1 illustrates an example system that delivers a cross-linking agent and photoactivating light to a cornea of an eye in order to generate cross-linking of corneal collagen, according to aspects of the present disclosure.

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. Pat. No. 10,342,697, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address corneal ectatic disorders, such as keratoconus or post-LASIK ectasia. Additionally, the application of riboflavin and the photoactivating light may to allow for various amounts of refractive correction, which for instance, may involve combinations of myopia, hyperopia, astigmatism, irregular astigmatism, presbyopia and complex corneal refractive surface corrections due to corneal ectatic disorders as well as other conditions of corneal biomechanical alteration/degeneration, etc.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110 is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined.

This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference. Embodiments may generate cross-linking activity in the cornea according to circular and/or annular patterns defined by the delivery of photoactivating light (e.g., via the DMD described above). Additionally or alternatively, embodiments may generate cross-linking activity in the cornea according to non-circular and/or non-annular patterns defined by the delivery of photoactivating light (e.g., via the DMD).

Patterns of photoactivating light can be applied (e.g., via the DMD) to the eye in separate treatment zones with different doses sequentially or continuously applied. For instance, one treatment zone can be "turned off" (i.e., delivery of the corresponding photoactivating light ceases) while another "stays on" (i.e., delivery of the corresponding photoactivating light continues). The treatment zones can be, for instance, annularly shaped about a center point of the eye. There may also be discontinuous zones where no the photoactivating light is applied (e.g., a central treatment zone surrounded by an annulus of no light surrounded by an annular treatment zone of light, etc.). The widths of the annular zones can be of different dimensions, e.g., one annular zone has a width of 1 mm and another has a width of 2 mm Applying the photoactivating light in annular treatment zones on the periphery of the eye without a central treatment zone can result in a hyperopic correction, for instance, by causing the central region of the eye to have an increased curvature while the periphery is strengthened. In some cases, central and surrounding treatment zones can be elliptical in shape, for instance to address astigmatism, by preferentially generating cross-linking activity in regions of the cornea to correct the astigmatism. Such elliptically shaped annular treatment zones are preferentially oriented with the axis of the annular treatment zones aligned according to the orientation of the astigmatism. The elliptically shaped treatment zones can also be irregularly asymmetric (i.e., having major and minor axis that are not perpendicular and can be situated with distinct center points (centers of mass)).

Cross-linking treatments can be tuned according to one or more biomechanical properties of the eye, such as the corneal topography (i.e., shape), corneal strength (i.e., stiffness), and/or corneal thickness. Optical correction and/or strengthening of the cornea can be achieved by applying the cross-linking agent and/or photoactivating light in one or more iterations with adjustable characteristics for each iteration. Generally, a developed treatment plan can include a number of applications of the cross-linking agent, the amount and concentration of the cross-linking agent for each application, the number of applications of photoactivating light, and the timing, duration, power, energy dosage, and pattern of the photoactivating light for each application. Furthermore, the cross-linking treatments can be adapted based on feedback information relating to the biomechanical properties gathered in real-time during treatment or during breaks in treatments.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Pat. No. 9,707,126, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 3, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

There have been attempts to develop a biochemical model that describes a set of chemical reactions induced by photoactivation of riboflavin in corneal cross-linking treatments. The development of earlier models arose from the introduction of accelerated cross-linking protocols. Originally, the evaluation of such protocols was based on the Bunsen-Roscoe law (BRL). According to the BRL, a certain photobiological effect is directly proportional to the total energy dose irrespective of the administered regime. The BRL, however, overestimates significantly the efficacy of accelerated cross-linking, and a nonlinear cross-linking theory is required.

The first variant of a nonlinear model of cross-linking was based on a polymerization model (PM). According to the PM, cross-linking is a light-induced polymerization process with an initiation rate (production rate of monomers) proportional to the volumetric absorption rate of UV-A light in the conical stroma. This model leads to the conclusion that cross-linking production rate is proportional to the square root of irradiance, in contrast to the BRL where the production rate must be proportional to irradiance. The PM explains the previous empirical finding that an accelerated protocol requires larger light dose for providing the same stiffening effect as the Dresden protocol. The PM was further developed to include the effect of light absorption on the concentration dynamics of riboflavin.

A downside of the PM, however, is that it ignores the key effect of oxygen on cross-linking rate. Under typical conditions (e.g., without an oxygen mask), the cross-linking rate is limited by oxygen rather than light. The oxygen effect was first considered by a biochemical model described in Kamaev et al., "Photochemical Kinetics of Corneal Cross-Linking with Riboflavin," *Investigative Ophthalmology & Visual Science*, April 2012, vol. 51, no. 4, pp. 2360-2367, and incorporated into U.S. Pat. No. 9,707,126. In particular, this model described two photo-biochemical pathways for riboflavin photoactivation, Type I and Type II, with the following reactions:

Common Reactions:

$$Rf \rightarrow Rf_1^*, I; \quad (r1)$$

$$Rf_1^* \rightarrow Rf, K1; \quad (r2)$$

$$Rf_1^* \rightarrow Rf_3^*, K2; \quad (r3)$$

Type I Reactions:

$$Rf_3^* + DH \rightarrow RfH^{\cdot} + D^{\cdot}, K3; \quad (r4)$$

$$2RfH^{\cdot} \rightarrow Rf + RfH_2, K4; \quad (r5)$$

Type II Reactions:

$$Rf_3^* + O_2 \rightarrow Rf + O_2^1, K5; \quad (r6)$$

$$DH + O_2^1 \rightarrow D_{ox}, K6; \quad (r7)$$

$$D_{ox} + DH \rightarrow D\text{-}D, K7; CXL \quad (r8)$$

In the reactions described herein, Rf represents riboflavin in the ground state. $Rf_1^*$ represents riboflavin in the excited singlet state. $Rf_3^*$ represents riboflavin in a triplet excited state. $Rf^-$ is the reduced radical anion form of riboflavin. $RfH^{\cdot}$ is the radical form of riboflavin. $RfH_2$ is the reduced form of riboflavin. DH is the substrate. $DH^{+\cdot}$ is the intermediate radical cation. $D^{\cdot}$ is the radical. $D_{ox}$ is the oxidized form of the substrate.

Riboflavin is excited into its triplet excited state $Rf_3^*$ as shown in reactions (r1) to (r3). From the triplet excited state $Rf_3^*$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UV-A irradiance and temperature and quickly decreases at the beginning of UV-A exposure. Utilizing pulsed light of a specific duty cycle, frequency, and irradiance, input from both Type I and Type II photo-biochemical mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, other substances or additives that affect the reaction and cross-linking rates may be applied to the cornea.

If UV-A radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photo-biochemical mechanisms for riboflavin photosensitization. Moreover, these parameters can be selected in such a way as to achieve a more optimal chemical amplification effect.

The biochemical model based on reactions (r1)-(r8) above generally focuses on oxygen dynamics and does not include equations for cross-link concentration. A simplified variant of this model provides approximate analytical expressions for concentrations of reagents including cross-links. Based on this simplified variant, cross-links are obtained by oxygenation of corneal radicals (both collagen and non-collagenous proteins) by singlet oxygen.

Another biochemical model (referred hereinafter as BCM) has been further developed to include an extended set of reactions, which account for additional cross-linking generation (both oxygen mediated and without oxygen) and the riboflavin aggregation process. Thus, a model of riboflavin diffusion in the presence of chemical reactions and aggregation is introduced. In addition to the reactions (r1)-(r8) above, the BCM includes the following reactions (r9)-(r26) which also occur during riboflavin photoactivation:

$$Rf_3^* = Rf, \kappa 8; \tag{r9}$$

$$Rf_3^* + Rf \rightarrow 2RfH; \kappa 9; \tag{r10}$$

$$RfH_2 + O_2 \rightarrow RfH + H^+ + O_2^{-1}, \kappa 10; \tag{r11}$$

$$RfH + O_2 \rightarrow Rf + H^+ + O_2^-, \kappa 11; \tag{r12}$$

$$2RfH + O_2^- \rightarrow 2RfH + H_2O_2, \kappa 12; \tag{r13}$$

$$2RfH + O_2^- \rightarrow 2Rf + H_2O_2, \kappa 13; \tag{r14}$$

$$RfH + H_2O_2 \rightarrow OH^\cdot + Rf + H_2O, \kappa 14; \tag{r15}$$

$$OH^\cdot + DH \rightarrow D^\cdot + H_2O, \kappa 15; \tag{r16}$$

$$D^\cdot + D^\cdot \rightarrow D-D, \kappa 16; CXL \tag{r17}$$

$$O_2^1 \rightarrow O_2, \kappa 18; \tag{r18}$$

$$D^\cdot + RfH_2 \rightarrow RfH + DH, \kappa 19; \tag{r19}$$

$$Rf + Rf \underset{\kappa_a^-}{\overset{\kappa_a^+}{\rightleftharpoons}} A_1, \kappa_a = \kappa_a^+/\kappa_a^- \tag{r20}$$

$$RfH_2 + RfH_2 \underset{\kappa_a^-}{\overset{\kappa_a^+}{\rightleftharpoons}} A_2, \kappa_a = \kappa_a^+/\kappa_a^- \tag{r21}$$

$$Rf + RfH_2 \underset{\kappa_b^-}{\overset{\kappa_b^+}{\rightleftharpoons}} A_3, \kappa_b = \kappa_b^+/\kappa_b^- \tag{r22}$$

$$Rf_1^* + A \rightarrow Rf + A, \kappa_{1a} \tag{r23}$$

$$Rf_3^* + A \rightarrow Rf + A, \kappa_{3a} \tag{r24}$$

$$2O_2^- \rightarrow O_2 + H_2O_2, \kappa_{12} \tag{r25}$$

$$OH^\circ + CXL \rightarrow \text{inert products}, \kappa_{OH} \tag{r26}$$

Figure 2A:
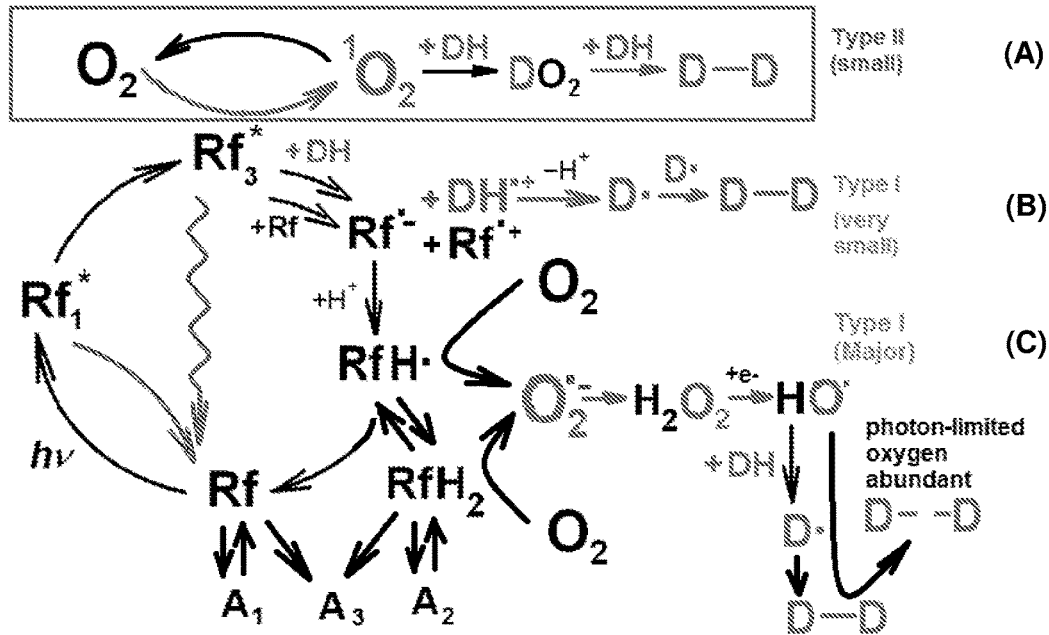
FIGS. 2A-B illustrate a diagram for photo-biochemical reactions involving riboflavin and photoactivating light (e.g., ultraviolet A (UV-A) light) applied during a corneal cross-linking treatment, according to aspects of the present disclosure.
Figure 2B:
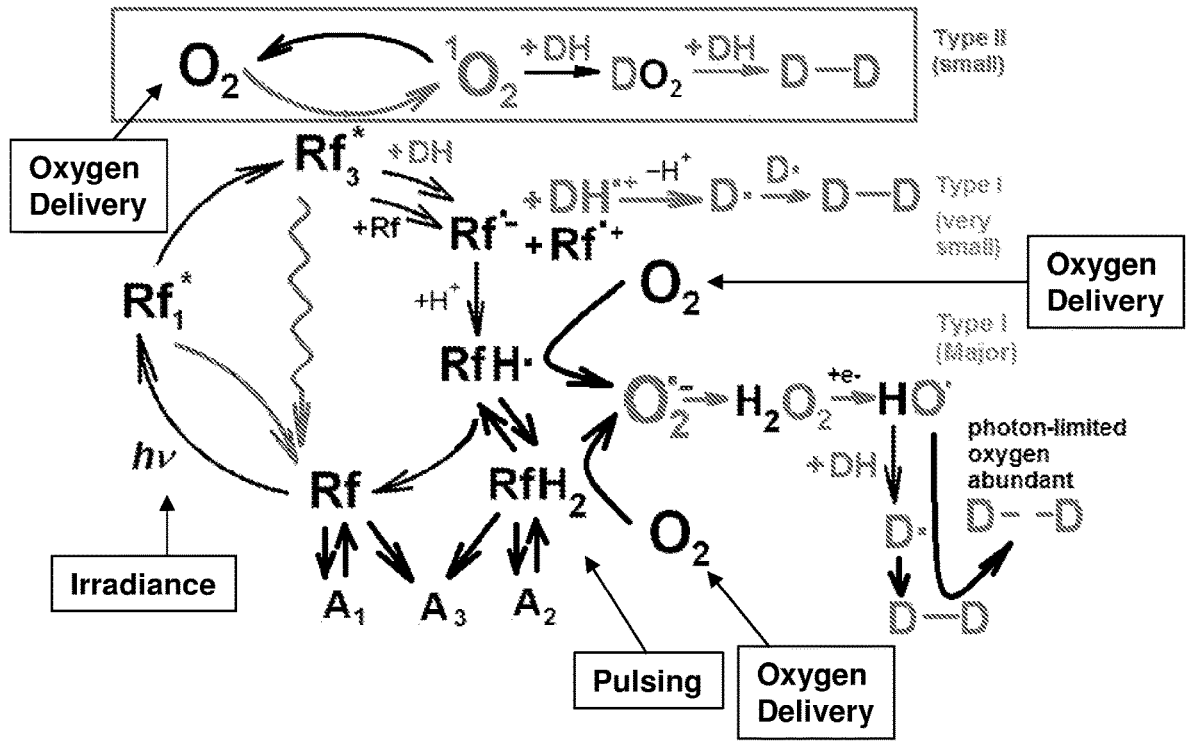

FIG. 2A illustrates a diagram for the photo-biochemical reactions provided in reactions (r1) through (r26) above. The diagram summarizes photochemical transformations of riboflavin (Rf) under UV-A photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals ($^\cdot OH$) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Indeed, where singlet oxygen plays a smaller role in generating cross-linking activity, some models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

The set of biochemical reactions yielding cross-linking activity occurs in the moving zone between aerobic (adjacent to corneal anterior surface) and anaerobic domains of corneal stroma. At the onset of UV-A illumination, the reaction zone appears just next to the anterior surface and moves towards the posterior surface as far as corneal radicals deplete. In the aerobic domain the formation of cross-links is complete, and the corresponding chemical reactions have stopped. Ambient oxygen diffuses freely through the aerobic domain towards the reaction zone where cross-linking occurs. The reactions consume oxygen and generate cross-links while the reaction site moves deeper into tissue. The anaerobic domain is located next to the reaction site and the oxygen supply to this domain is blocked while an appreciable UV-A illumination is still present. The formation of cross-links proceeds here in anaerobic mode at a very slow rate. Further aspects of the biochemical reactions provided by the BCM are described in U.S. Pat. No. 10,350,111, filed Apr. 27, 2016 and titled "Systems and Methods for Cross-Linking Treatments of an Eye," the contents of which are incorporated entirely herein by reference.

A large variety of factors affect the rate of the cross-linking reaction and the amount of biomechanical stiffness achieved due to cross-linking. A number of these factors are interrelated, such that changing one factor may have an unexpected effect on another factor. The BCM provides a more comprehensive model for understanding the relationship between different factors for cross-linking treatment based on the photo-biochemical reactions (r1)-(r26) identified above. Accordingly, systems and methods can adjust various parameters for cross-linking treatment according to the BCM, which provides a unified description of oxygen dynamics and cross-linking activity. The BCM can be employed to evaluate expected outcomes based on different combinations of treatment parameters and to identify the combination of treatment parameters that provides the desired result. The parameters, for example, may include, but is not limited to: the concentration(s) and/or soak times of the applied riboflavin; the dose(s), wavelength(s), irradiance(s), duration(s), and/or pulse dynamics of the photoactivating light; the oxygenation conditions in the tissue; procedure duration; spatial geometry; and/or presence of additional agents and solutions. For instance, the BCM can combine these parameters as inputs with chemical reaction rates expressed as a function of the reactant species concentrations to model the biochemical dynamics required to estimate a three-dimensional cross-linking concentration profile in the cornea. The biochemical dynamics of the cross-linking procedure can be modeled using either finite difference or finite element method.

Cross-linking activity results in a change in the cornea's biomechanical properties by altering the balance between the internal stresses in the cornea and the eye's intraocular pressure (IOP). The change in biomechanical properties causes the cornea to deform. Because the cornea accounts for much of the eye's total optical power, a deformation of the cornea results in a change in the patient's vision. Corneal cross-linking treatments can therefore be employed to impart a vision change via a choice of treatment parameters, taking into account the pre-treatment characteristics of the patient's eye.

Figure 3:
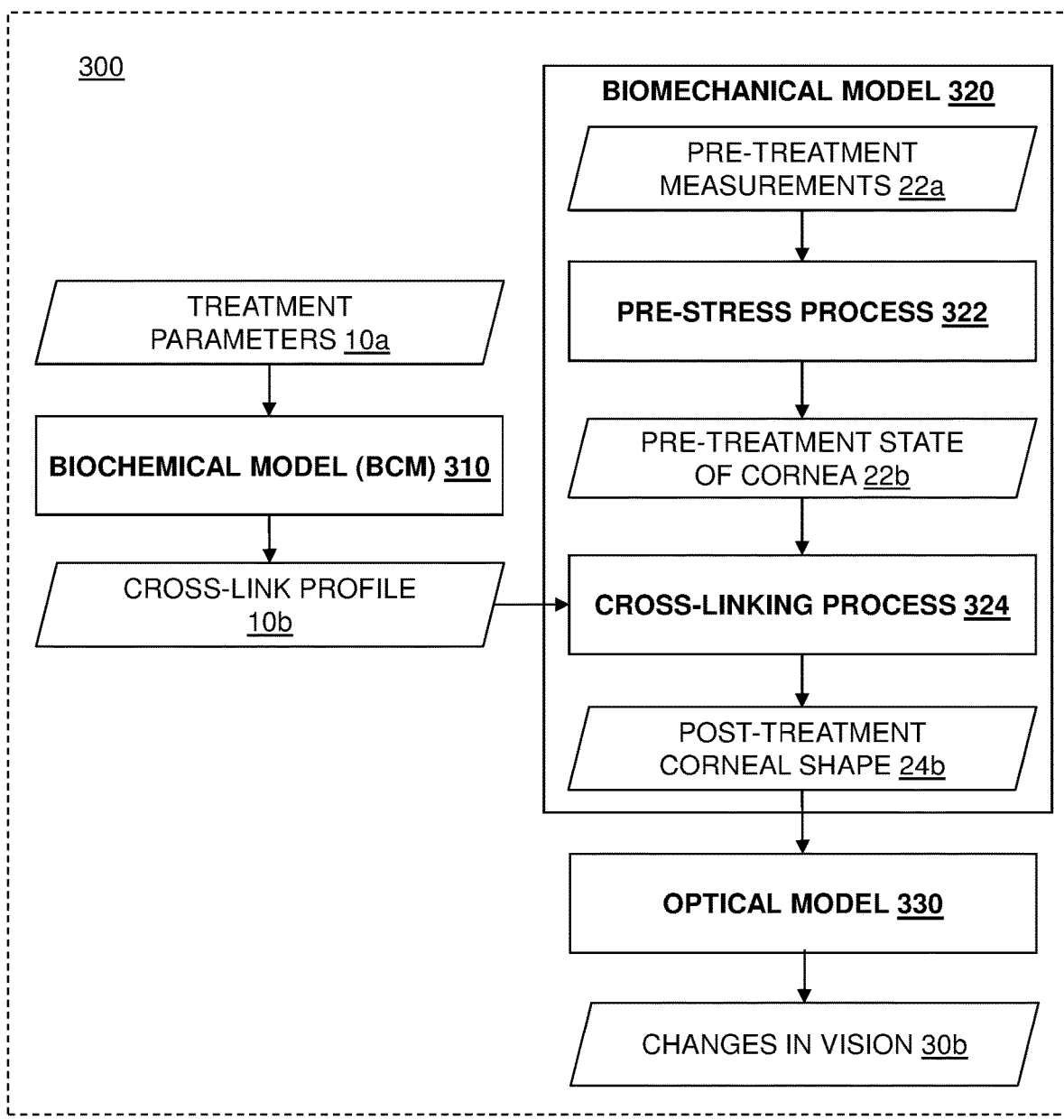
FIG. 3 illustrates an example modeling system including a combination of a biochemical model, a biomechanical model, and an optical model to make patient-specific determinations of outcomes from corneal cross-linking treatments, according to aspects of the present disclosure.

To choose an optimal configuration of treatment parameters to optimize treatment outcomes and/or to accurately determine the outcome of a particular cross-linking treatment, the process involves an understanding of: (1) the photo-biochemical dynamics of the cross-linking reaction; (2) the biomechanically induced cornea remodelling; and (3) the corresponding refractive changes in the optic power of the treated eye. As such, as shown in FIG. 3, the BCM 310 can be combined in a modeling system 300 with a biomechanical model 320 and an optical model 330 to make patient-specific determinations of outcomes from corneal cross-linking treatments. The modeling system 300, for instance, can determine (1) the distribution of cross-links in the cornea, (2) the induced corneal shape change, and (3) the impact on the patient's vision.

As described above, the BCM 310 models a cross-linking treatment as a set of chemical reactions in the corneal stroma induced by UV-A light. The corresponding biochemical dynamics can be modeled using either finite difference or finite element method. The input 10a for the BCM 310 includes a set of parameters for the treatment protocol, such as soak time for the cross-linking agent, light pulse duration, light irradiance, light dose, illumination pattern, and/or $O_2$ concentration, etc. The output 10b provides profiles of all the reagents including a cross-link profile during and after the treatment.

Meanwhile, the biomechanical model 320 determines the structural remodeling of the cornea (i.e., shape change) caused by tissue stiffening associated with new cross-links formed at the treatment site. The biomechanical model 320 employs a hyperelastic corneal model. According to the hyperelastic corneal model, strain energy density includes an isotropic contribution from bulk stromal tissue and an anisotropic contribution from collagen fibril network. The collagen fibril network includes two sets of fibrils that are orthogonal in the central part of eye and are oriented circumferentially as they extend along the periphery of the eye.

The biomechanical model 320 can process the pre-treatment corneal shape of a patient obtained by means of eye topography. The parameters for the pre-treatment corneal stiffness can be adjusted, for instance, according to patient age or in vivo measurements of corneal strength. The pre-treatment geometry of an eye is obtained under a certain IOP. The biomechanical model 320 can be implemented using a finite element method where the constitutive relations of the model are used to calculate the stress profile in the stroma. The boundary conditions at the anterior surface are such that it is free to move whereas the posterior surface is under the pressure of the IOP.

Although aspects of a particular hyperelastic corneal model may be described herein, it is understood that other hyperelastic models may be contemplated and employed. Additionally, the constitutive model of corneal tissue may include both elasticity and viscosity.

The biomechanical model 320 includes pre-stress processing 322 and cross-linking processing 324. The pre-stress processing 322 determines a pre-treatment state of the cornea, where intraocular pressure (IOP) at the corneal posterior surface is balanced by a field of stress tensor in the corneal material frame. The input 22a for the pre-stress processing 322 includes pre-treatment corneal shape (e.g., three-dimensional shape) and a pre-treatment IOP measured prior to the cross-linking treatment, and the output 22*b* is the pre-treatment state of the cornea.

Methods relating to pre-stress processing can be found, for instance, in J. Bols et al., "A computational method to assess the in vivo stresses and unloaded configuration of patient-specific blood vessels," *J. Computational and Applied Mathematics,* 246 (2013), 10-17; Hannah Weisbecker, et al., "A generalized prestressing algorithm for finite element simulations of preloaded geometries with application to the aorta." *Int. J. Num. Meth. Biomed. Eng.,* 2014, 30:857-872; and Rafael Grytz et al., "A Forward Incremental Prestressing Method with Application to Inverse Parameter Estimations and Eye-Specific Simulations of Posterior Scleral Shells," *Comput. Methods Biomech. Biomed. Engin.,* July 2013, 16(7): 768-780. For instance, pre-stress processing developed for artery walls can be applied to corneal shape evaluation.

According to one approach, pre-stress processing may involve modeling the cornea in an unloaded and unstressed state (i.e., no force applied and no internal stress), where the cornea deforms to its pre-treatment geometry when the application of IOP is simulated. This, however, is a computationally expensive approach requiring many iterations to change the model geometry.

Advantageously, the pre-stress processing 322 employs a less computationally expensive approach, which can be executed at faster speeds. According to this alternative approach, at a first iteration, the IOP is set to the measured pre-treatment IOP and the initial stress tensor in the corneal material frame is set to zero. The application of the model yields an updated stress tensor field and the corresponding displacement field. For the next iteration, the displacement field is set to zero but the internal stress tensor field carries forward. The model is reapplied yielding further updates to the internal stress tensor field and displacement field. Again, the displacement field is set to zero and the new updated stress tensor field is carried forward to the next iteration. The pre-stress processing 322 continues to iterate until the root mean square (RMS) of the displacement field falls below a threshold value. The threshold value for the displacement is much lower than a typical displacement due to a cross-linking treatment. For instance, it can be set to a few tenths of a micrometer. If the displacement field starts to increase, the pre-stress processing 322 is restarted (setting the stress tensor field to zero) with an initial IOP which is less than the measured pre-treatment IOP. Then, for each iteration, the IOP is increased up to the point that it reaches the originally measured pre-treatment IOP. The pre-stress processing 322 fails if the number of iterations exceeds a predefined number. Using this alternative approach, the internal corneal stress in the pre-treatment state can be determined using the pre-treatment corneal geometry without any need to make calculations for an unloaded and unstressed corneal state.

Following the pre-stress processing 322, the cross-linking processing 324 determines the remodeling of the cornea (the post-treatment corneal shape) caused by the application of the cross-linking treatment. The new cross-links increase corneal stiffness, altering the balance between the internal stress and IOP. The elasticity parameters of the stroma are increased as functions of the cross-link concentration. As shown in FIG. 3, the three-dimensional distribution of cross-links in the stroma can be derived from the BCM 310 as the output 10*b* (or alternatively, from a direct measurement method (e.g., densitometry, OCT, fluorescence)). The constitutive relations of the elasticity model are used for the recalculation of the stress profile in stroma. The updated stress profile does not balance the IOP at the posterior surface and the model therefore yields the post-treatment corneal shape. As a result, the cornea transitions from a pre-treatment to post-treatment shape where a new balance between internal stress and IOP is established. The input for the cross-linking model 324 includes the cross-link profile from the BCM 310 and the pre-treatment state of the cornea (pre-treatment corneal shape, pre-treatment elasticity of the cornea, a pre-treatment stiffness profile, and pre-treatment IOP) from the pre-stress processing 322. The cross-linking processing 324 also employs a set of parameters describing the dependence of corneal stiffness on the cross-link concentration. The output 24*b* for the cross-linking model 324 provides the post-treatment corneal shape.

It is noted that embodiments can account for the effect of eye motion during cross-linking treatment. Eye motion affects the changes of eye shape during the cross-linking treatment. Taking eye motion into account is notable when the light spot assumes a complex shape, e.g., annulus shape used for the treatment of hyperopic and presbyopic patients. The embodiments in such cases can optimize the illumination pattern for the correction of certain defects of vision.

The optical model 330 is a ray trace model of image formation on the retina. Both the pre-treatment eye and the post-treatment eye are modeled and changes in patient refraction and corrected and uncorrected visual acuity can be determined as output 30*b*. Optical models may involve a single refractive surface (reduced eyes), three refractive surfaces (simplified eyes), or more than three surfaces which may be aspherical. The most advanced models allow for spatial variations in the refractive index of the crystalline lens. Simple paraxial models are capable of determining retinal image quality only if the pupil size is small and the object is close to optical axis. Finite optical models can be employed if the pupil size is large and the object is at the periphery of the field of view. The models of the latter type may be either sequential or non-sequential. The sequential models allow optical rays to propagate through the optical surfaces in a prescribed order only—no stray light analysis is possible. Such models are useful for the image quality evaluation and the analysis of aberrations. The nonsequential models allow rays to propagate through the surfaces in any order and may be used for illumination, stray light, scattering, and fluorescence analysis. Related descriptions can be found, for instance, in D. A. Atchinson, "Optical models of human myopic eyes," *Vision Research* 46 (2006) 2236-2250; D. A. Atchinson et al., "Optical models of the human eye," *Clin Exp Optom* 2016, 99: 99-106; D. A. Atchinson et al., *Optics of the Human Eye,* 1st Edition, Butterworth-Heinemann 2000; and Rod Watkins, "Zemax Models of the Human Eye," published Dec. 17, 2013 at Zemax customer portal.

According to one embodiment, the optical model 330 employs a finite optical model with five surfaces (including retina), which may be aspherical in either sequential or non-sequential implementation. The optical model 330 can be developed with ray trace software. The optical model 330 can be modified to include optical components to simulate eye exams; in particular, the exam for sphere is modeled in the presence of a corrective lens. The front surface of the cornea is modeled as an extended polynomial surface (an ellipsoid shape plus residuals extrapolated as a two dimensional polynomial). The latter surface type is compatible with the elastic model of the eye. Thus, patient specific shapes of the anterior corneal surface can be transferred from the biomechanical model 320 as input to the ray trace model for the analysis of optical outcomes. The output 30*b* of the optical model 330 can be used in the evaluation of manifest refraction spherical equivalent (MRSE) and visual acuity. Advantageously, the optical model 330 allows one to gain insight into vision correction studies based on cross-linking treatments.

Accordingly, the three models can be integrated into a single modeling system 300, whereby the output from the BCM 310 is processed by the biomechanical model 320 which in turn provides the input for the optical model 330. The modeling system 300, given a set of inputs and parameters, can determine keratometric changes and visual function changes. In addition, the modeling system 300 can be used to optimize treatment parameters in order to achieve desired clinical results. Advantageously, the integration of the three models 310, 320, 330 makes it possible to perform the analysis of shape changes and optical outcomes in terms of treatment protocol more efficiently. In particular, the use of the biochemical model eliminates any need to use speculative profiles of cross-link concentration for the biomechanical model. Such integration minimizes any operator involvement in the processes for calibration, analysis, and report generation, thereby minimizing the introduction of human error. Time intensive tasks (calibration and analysis using large data sets including the generation of the proper reports) can be performed automatically in less processing time, without any intervening involvement by the operator. In some embodiments, aspects of the three models may operate in parallel and output data from the different models can undergo parallel processing. This feature is useful for performing time consuming tasks like model calibration with measured optical data.

Figure 4A:
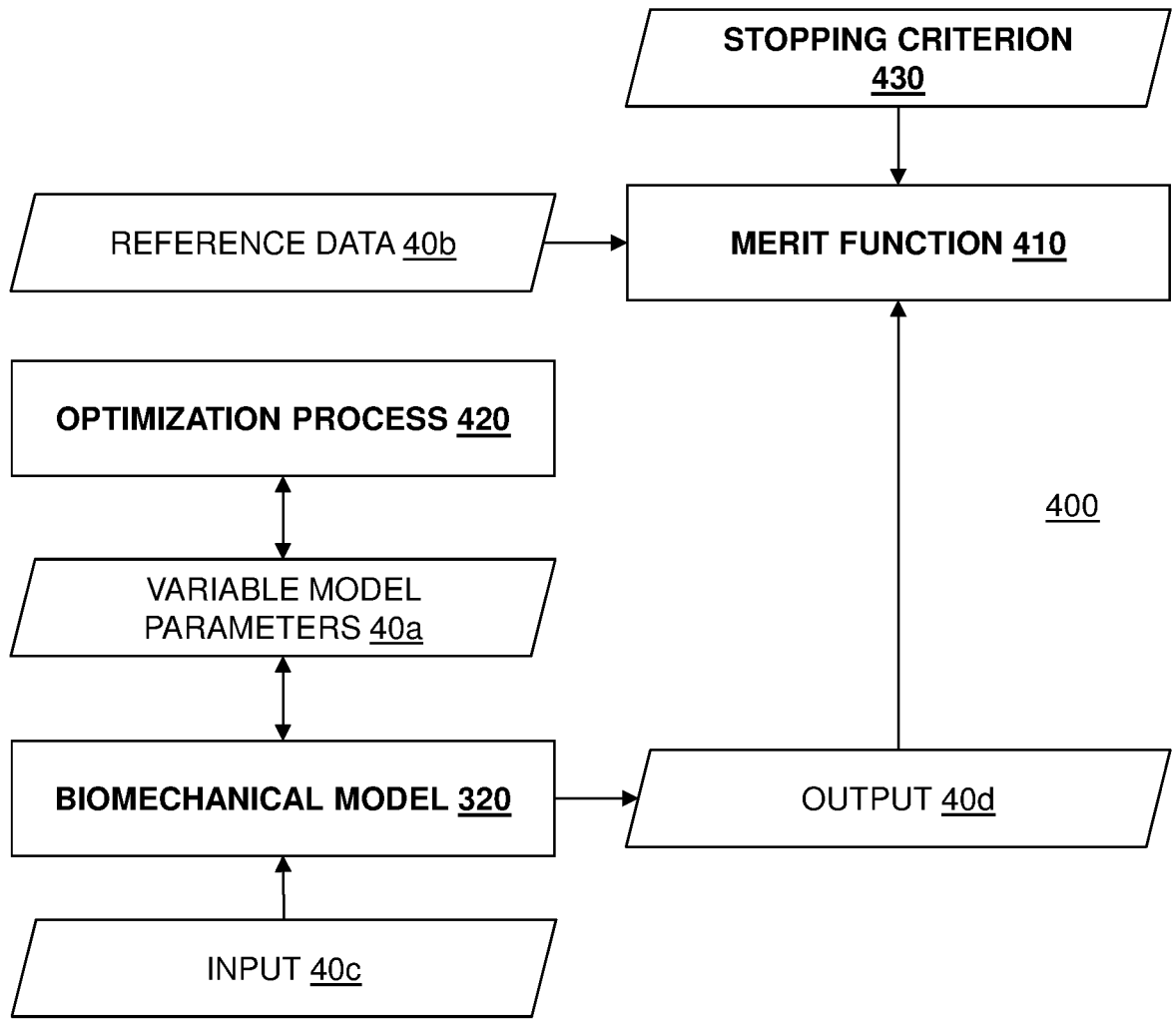
FIG. 4A illustrates an example calibration procedure for aspects of a modeling system, according to aspects of the present disclosure.

Aspects of the present disclosure may also employ a calibration procedure whereby parameters related to the elasticity of the stromal matrix and fibers and the stiffening effect of the cross-linking are derived using measured data. FIG. 4A illustrates aspects of an example calibration procedure 400 for the biomechanical model 320. The calibration procedure 400 evaluates and calibrates variable model parameters 40a describing nonlinear corneal elasticity and their change during a cross-linking treatment in view of measured reference data 40b. Generally, the calibration procedure 400 includes a merit function 410, an optimization process 420, and a stopping criterion 430. The biomechanical model 320 receives input 40c and uses a current set of model parameters 40a to generate output 40d. The merit function 410 compares the output 40d to the measured reference data 40b. At iteration n=0, the variable model parameters 40a are set to some initial values. The optimization step 420 updates the model parameters 40a during subsequent iterations n=n+1 such that the merit function 410 reduces to the point where the stopping criterion 430 is met. If the iteration number exceeds a predefined threshold, calibration fails.

Figure 4B:
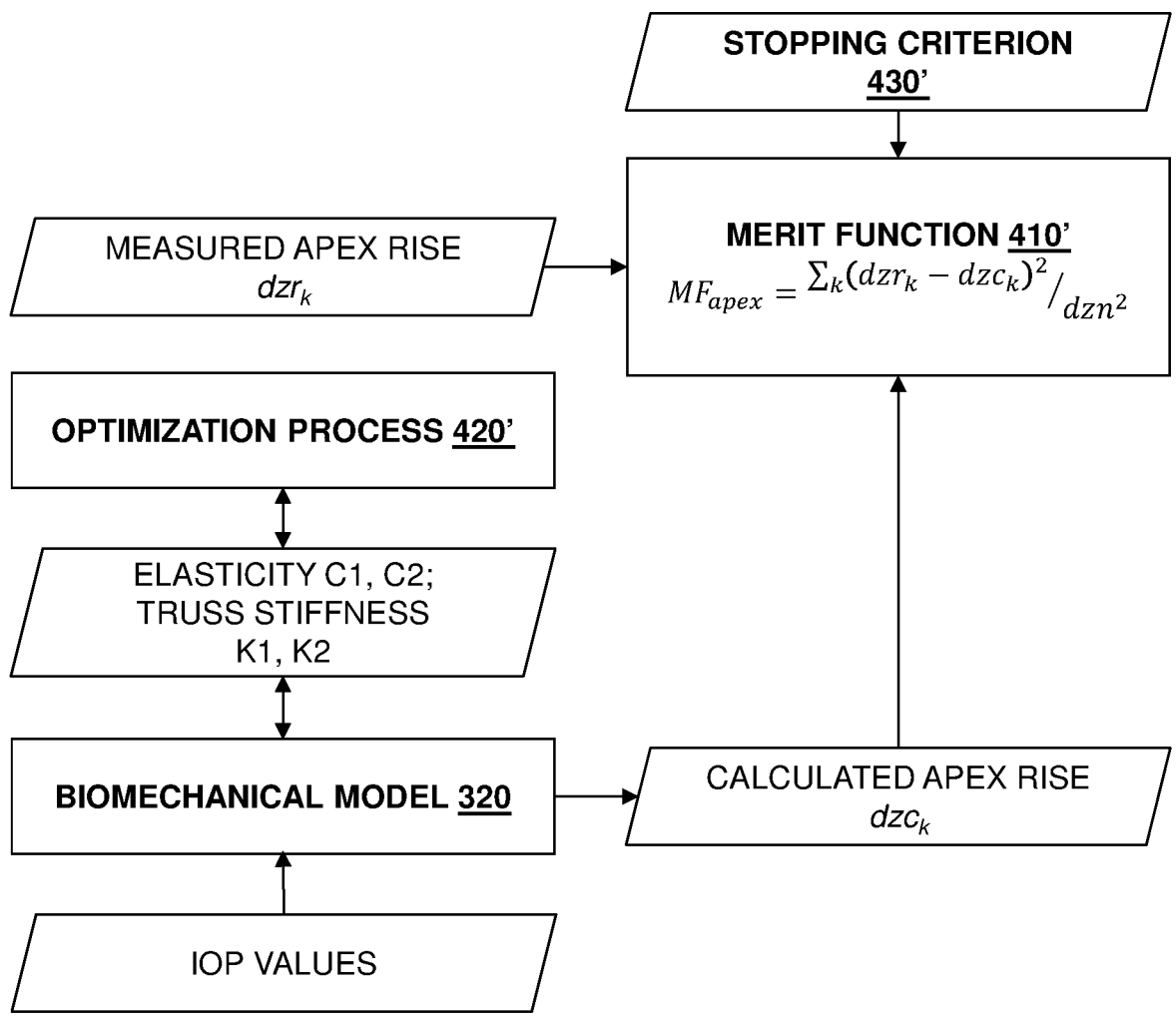
FIG. 4B illustrates the example calibration procedure of FIG. 4A applied in the first of two phases for a biomechanical model, according to aspects of the present disclosure.
Figure 4C:
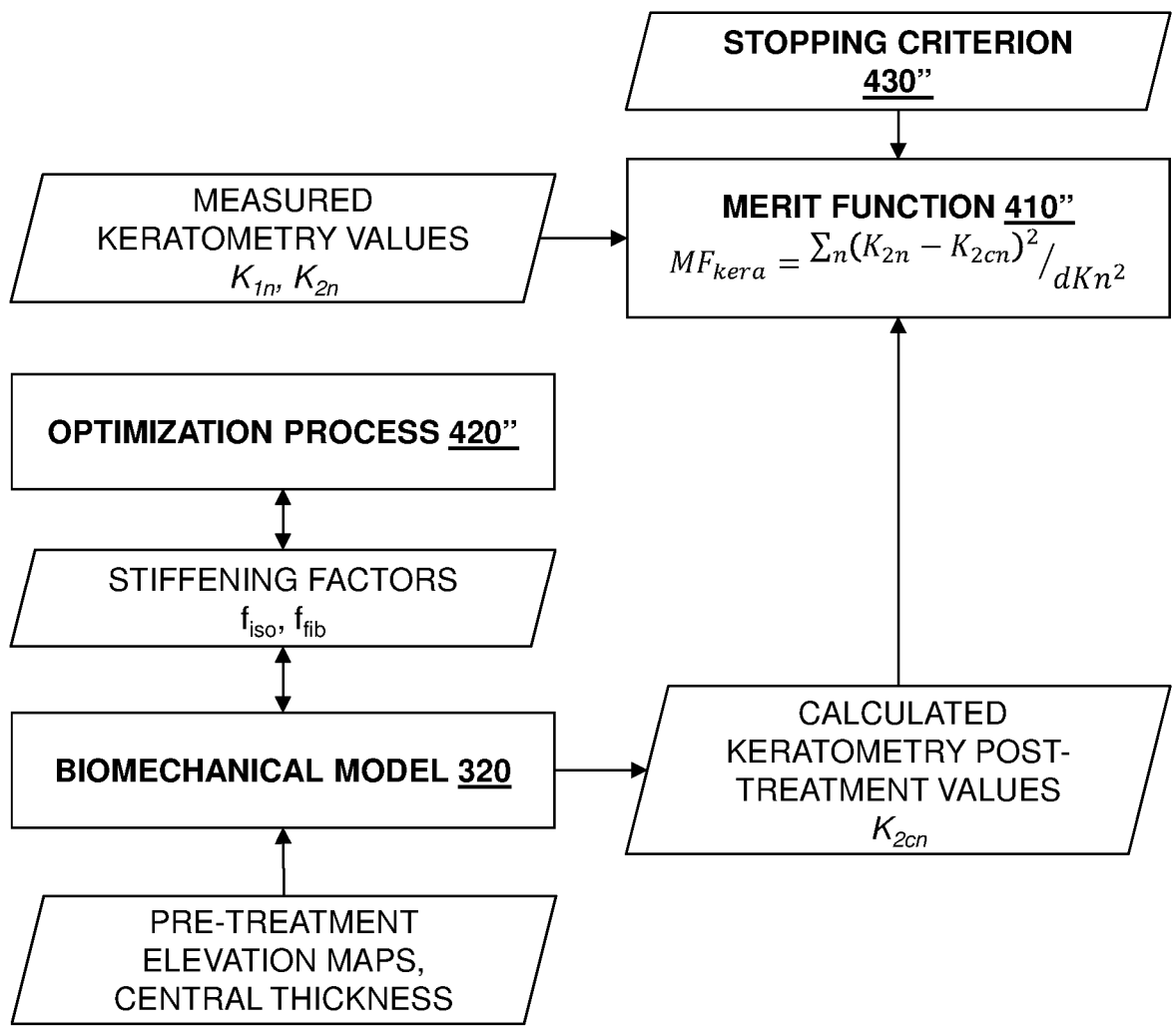
FIG. 4C illustrates the example calibration procedure of FIG. 4A applied in the second of two phases for a biomechanical model in connection with FIG. 4B, according to aspects of the present disclosure.

In some embodiments, the calibration procedure 400 for the biomechanical model 320 may be applied in two phases as shown in FIGS. 4B-C, respectively:

Phase 1—Calibration of Internal Elasticity Parameters

As FIG. 4B illustrates, the calibration procedure 400 employs a merit function 410', an optimization process 420', and a stopping criterion 430'. As described above, the hyperelastic model models the corneal stroma as a mix of isotropic material and the collagen fibril network. The strain energy is a sum of contributions of both components. The isotropic contribution is described by elasticity parameters $C_1$ and $C_2$. The anisotropic contribution is defined by the truss stiffness parameters $K_1$ and $K_2$. This phase determines the internal elasticity parameters using suitable reference data. In one embodiment, the calibration procedure uses an apex inflation dataset of a typical eye or a set of eyes. The list of variable parameters is ($C_1$, $C_2$, $K_1$, $K_2$). The input data for the biomechanical model 320 is a list of intraocular pressures (IOP) used in the measurements of apex rise. The reference data includes the measured rises of apex, $dzr_k$, where index k is the number of a measurement. The output data of the biomechanical model 320 includes the calculated rises of apex, $dzc_k$, at the same IOP values. The merit function 410' is $MF_{apex}=\Sigma_k(dzr_k-dzc_k)^2/dzn^2$, value of apex rise, dzn, is used for normalization.

Although embodiments may employ eye inflation—apex rise data for calibration, other datasets may be contemplated and employed for the determination of the elastic properties of patient groups chosen for calibration.

In another embodiment, the reference data includes ex vivo or in vivo measurements of corneal strength/stiffness and/or deformations of the cornea as perturbed by different dynamic forces. The output of this calibration procedure includes the model stiffness parameters that characterize the biomechanical properties of the cornea prior to the application of the cross-linking procedure.

Phase 2—Calibration of Cross-Linking Factors

As FIG. 4C illustrates, the calibration procedure 400 employs a merit function 410", an optimization process 420", and a stopping criterion 430". The second phase of the calibration procedure determines the stiffening factors associated with the introduction of cross-links in the collagen. In this phase, the fixed model parameters include the three-dimensional distribution of cross-links in the stroma as derived from the BCM 310 described above or from a direct measurement method (e.g., densitometry, OCT, fluorescence). The reference data includes sets of corneal topographies measured pre- and post-treatment. The generation of cross-links increases $C_1$ and $C_2$ by stiffening factor $(1+f_{iso} CXL/CXL_{max})$ while $K_1$ is increased by stiffening factor $(1+f_{fib} CXL/CXL_{max})$ where CXL and $CXL_{max}$ are local and saturated concentrations of cross-links, respectively. It is assumed that parameter $K_2$ does not change. The stiffening factors $f_{iso}$ and $f_{fib}$ are the variable model parameters which are updated during the calibration procedure. The merit function 410" compares the model calculations for corneal shape with the measured reference data. In one embodiment, both pre-treatment, $K_{1n}$, and post-treatment, $K_{2n}$, keratometry values measured with a corneal topographer form a set of reference data, with n being a number of an eye. The corresponding input data for the biomechanical model 320 is a set of pre-treatment elevation maps (for both corneal surfaces) and pre-treatment values of central thickness of the same eyes. The output data for the biomechanical model 320 is a set of calculated post-treatment keratometry values, $K_{2cn}$. The merit function 410" is $MF_{kera}=\Sigma_n(K_{2n}-K_{2cn})^2/dKn^2$ with $dKn^2$ being an arbitrary normalization keratometry difference.

An alternative embodiment may combine the two calibration phases into one whereby the variable parameter of the calibration are $C_1$, $C_2$, $K_1$, $K_2$, $f_{iso}$, and $f_{fib}$ and the reference data is the set of pre- and post-treatment topographies of treated eyes. This calibration procedure is fully automated and may proceed without intervening involvement by an operator.

The calibration procedure allows the evaluation of model parameters (e.g., describing both tissue elasticity and stiffening under cross-linking) for providing best fit for a certain dataset (e.g., apex inflation measurements or data of clinical trials). This calibration procedure is advantageous because different patient groups (e.g., patients of different ages, patients having certain chronic deceases, etc.) exhibit different biochemical, elastic, and stiffening properties in their eyes. Such differences result in large variations in treatment results when the different patient groups are combined. The calibration module makes it possible to calibrate the model separately for different patient datasets and find best fit model parameters for different patient groups. Additionally, the automatic calibration is objective method that is more accurate than subjective comparison of the measured and calculated data.

Applications for the embodiments above may include:
analysis of clinical data;
prediction of treatment results;
separation of patient groups showing similar treatment results;
gaining further insight into basic mechanisms of cross-linking processes;
identifying correlations between inputs and outcomes for cross-linking processes; and/or
optimization of cross-linking protocols to get best results for different treatment types and patient groups.

As described above, according to some aspects of the present disclosure, some or all of the steps of the above-described and illustrated procedures can be automated or guided with a computing system or a controller (e.g., the controller 120). For instance, the models described herein may be implemented and integrated via a computing system. Generally, a computing system/controller may be implemented as a combination of hardware and software elements. The hardware aspects may include combinations of operatively coupled hardware components including microprocessors, logical circuitry, communication/networking ports, digital filters, memory, or logical circuitry. The computing system/controller may be adapted to perform operations specified by a computer-executable code, which may be stored on a computer readable medium.

The computing system/controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), microcontrollers, and the like, programmed according to the teachings of the example embodiments of the present disclosure, as is appreciated by those skilled in the computer and software arts. The physical processors and/or machines may be externally networked with the image capture device (s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of non-transitory computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such non-transitory computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. For instance, embodiments may employ Comsol software for finite element analysis, Zemax Optical Studio for optical raytrace, and Matlab software for user interface, pre-processing, and post-processing. However, different FEM and raytrace software packages may be employed. Additionally, Matlab programming language may be replaced by different programming languages, in particular, by Python or C++. Moreover, parts of the processing of the example embodiments of the present disclosure can be distributed for better performance, reliability, cost, and the like.

Common forms of non-transitory computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A system for corneal treatment for a subject, comprising:

an illumination system including a light source and optical elements, the illumination system configured to generate cross-linking in at least one selected region of a cornea treated with a cross-linking agent by delivering photoactivating light to the at least one selected region of the cornea according to one or more photoactivation parameters; and a controller configured to receive input relating to one or more treatment parameters, the one or more treatment parameters including the one or more photoactivation parameters, the controller configured to execute program instructions stored on one or more nontransitory computer-readable storage media to output information for adjusting the one or more treatment parameters, the program instructions including:

(A) a first set of program instructions that determines, from the input relating to the one or more treatment parameters, a distribution of cross-links for the at least one selected region of the cornea;

(B) a second set of program instructions the determines, from the distribution of cross-links, a shape change for the cornea; and (C) a third set of program instructions that determines, from the shape change for the cornea, a change in vision for the subject, wherein, in response to the output from the controller, the illumination system is configured to adjust at least one of the one or more photoactivation parameters for delivering the photoactivating light, and wherein the third set of program instructions determines the change in vision for the subject based on a ray trace model of image formation on a retina in response to the shape change for the cornea.

2. The system of claim 1, wherein the one or more treatment parameters includes at least one of a soak time for the cross-linking agent, a pulse duration for the photoactivating light, an irradiance of the photoactivating light, a dose of the photoactivating light, an illumination pattern for the photoactivating light, or a concentration of oxygen applied to the cornea.

3. The system of claim 1, wherein the first set of program instructions determines the distribution of cross-links from (i) reactions involving reactive oxygen species (ROS) including at least singlet oxygen, peroxides, superoxides, and hydroxyl radicals, and (ii) reactions not involving oxygen.

4. The system of claim 1, wherein the second set of program instructions determines (i) a pre-treatment state of the cornea based on a pre-treatment shape and a pre-treatment intraocular pressure of the cornea, and (ii) the shape change for the cornea based on the pretreatment state of the cornea and the distribution of cross-links.

5. The system of claim 1, further comprising an oxygen source and an oxygen delivery device configured to provide a concentration of oxygen from the oxygen source to the at least one selected region of the cornea, wherein the one or more treatment parameters further relates to the concentration of oxygen.

6. The system of claim 1, wherein the second set of program instructions determines the shape change for the cornea according to a biomechanical model that models corneal elasticity and a stiffening associated with cross-links.

7. The system of claim 6, wherein the controller is further configured to calibrate the biomechanical model by calibrating, based on measured reference data, variable model parameters relating to the corneal elasticity and the stiffening associated with cross-links.

8. The system of claim 7, wherein the variable model parameters include elasticity parameters associated with isotropic material in a stroma of the cornea and stiffness parameters associated with anisotropic material in the stroma, and the controller calibrates the elasticity parameters and the stiffness parameters according to measurements of apex rise associated with intraocular pressure.

9. The system of claim 7, wherein the variable model parameters include stiffening factors associated with cross-links, and the controller calibrates the stiffening factors according to measurements of keratometry.

10. One or more non-transitory computer-readable storage media, having program instructions stored thereon, wherein when executed by a controller, the computer-executable instructions cause the controller to:

receive input relating to one or more treatment parameters for generating crosslinking in at least one selected region of a cornea treated with a cross-linking agent;

determine, from the input relating to the one or more treatment parameters, a distribution of cross-links for the at least one selected region of the cornea; determine from the distribution of cross-links, a shape change for the cornea;

determine, from the shape change for the cornea, a change in vision for the subject, wherein the controller determines the change in vision for the subject based on a ray trace model of image formation on a retina in response to the shape change for the cornea; and output information for adjusting the one or more treatment parameters responsive to the determined change in vision for the subject.

11. The one or more non-transitory computer-readable media of claim 10, wherein the one or more treatment parameters include one or more photoactivation parameters, and the computer-executable instructions further cause the controller to cause an adjustment to at least one of the one or more photoactivation parameters for an illumination system, the illumination system configured to generate the cross-linking in the at least one selected region of the cornea by delivering photoactivating light to the at least one selected region of the cornea according to the one or more photoactivation parameters.

12. The one or more non-transitory computer-readable media of claim 10, wherein the one or more treatment parameters include a concentration of oxygen applied by an oxygen source and an oxygen delivery device to the at least one selected region of the cornea, and the computer-executable instructions further cause the controller to cause an adjustment to the concentration of oxygen applied by the oxygen source and the oxygen delivery device.

13. The one or more non-transitory computer-readable media of claim 10, wherein the controller determines the distribution of cross-links from (i) reactions involving reactive oxygen species (ROS) including at least singlet oxygen, peroxides, superoxides, and hydroxyl radicals, and (ii) reactions not involving oxygen.

14. The one or more non-transitory computer-readable media of claim 10, wherein the controller determines a pre-treatment state of the cornea based on a pre-treatment shape and a pre-treatment intraocular pressure of the cornea, and the shape change for the cornea based on the pre-treatment state of the cornea and the distribution of cross-links.

15. The one or more non-transitory computer-readable media of claim 10, wherein the controller determines the shape change for the cornea according to a biomechanical model that models corneal elasticity and a stiffening associated with cross-links.

16. The one or more non-transitory computer-readable media of claim 15, wherein the computer-executable instructions further cause the controller to calibrate the biomechanical model by calibrating, based on measured reference data, variable model parameters relating to the corneal elasticity and the stiffening associated with cross-links.

17. The one or more non-transitory computer-readable media of claim 16, wherein the variable model parameters include elasticity parameters associated with isotropic material in a stroma of the cornea and stiffness parameters associated with anisotropic material in the stroma, and the controller calibrates the elasticity parameters and the stiffness parameters according to measurements of apex rise associated with intraocular pressure.

18. The one or more non-transitory computer-readable media of claim 16, wherein the variable model parameters include stiffening factors associated with cross-links, and the controller calibrates the stiffening factors according to measurements of keratometry.

* * * * *